United States Patent [19]

Cavazza

[11] Patent Number: 4,602,039

[45] Date of Patent: Jul. 22, 1986

[54] SALTS OF-CARNITINE AND ALKANOYL L-CARNITINES AND PROCESS FOR PREPARING SAME

[75] Inventor: Claudio Cavazza, Rome, Italy

[73] Assignee: Sigma-Tau Industrie Farmaceutiche Riunite S.p.A., Rome, Italy

[21] Appl. No.: 680,380

[22] Filed: Dec. 11, 1984

[30] Foreign Application Priority Data

Dec. 28, 1983 [IT] Italy .............................. 49594 A/83
Nov. 6, 1984 [IT] Italy .............................. 49123 A/84

[51] Int. Cl.$^4$ ................. C07D 101/30; A61K 31/195
[52] U.S. Cl. .................................... 514/561; 314/529; 260/501.13
[58] Field of Search ................... 260/501.13; 514/561, 514/529

[56] References Cited

FOREIGN PATENT DOCUMENTS 2529545  1/1984  France ........................... 260/501.13

OTHER PUBLICATIONS

Chemical Abstracts vol. 75, (1971) Item 36096y, Abstracting Spanish Patent 366,137, 1 Feb. 1971.
Chemical Abstracts vol. 77, (1972) Item 33996, Abstracting Spanish Patent 373,432. 16 Jan. 1972.
Chemical Abstracts, vol. 79, (1973) Item 9915r, Abstracting Spanish Patent 328,806, 16 Jul. 1972.

*Primary Examiner*—Robert T. Bond
*Attorney, Agent, or Firm*—Bruce M. Collins

[57] ABSTRACT

Novel L-carnitine and alkanoyl L-carnitine salts and a process for their preparation are disclosed. The salts have the general formula

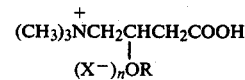

wherein
- $X^-$ is an anion of acid aspartate, acid citrate, acid phosphate, acid fumarate, lactate, acid maleate, acid oxalate, acid sulphate or orotate;
- R is hydrogen provided that $X^-$ is other than the orotate anion, or lower alkanoyl selected among acetyl, propionyl and butyryl; and
- n is ½ if $X^-$ is orotate, and 1 if $X^-$ is one of the other anions.

Since they are not hygroscopic, these salts can be easily compounded and are favorably suitable for manufacturing solid administration forms. Their aqueous solutions are less acid than those of the corresponding chlorides: consequently, these salts are also suitable for manufacturing injectable administration forms.

16 Claims, No Drawings

SALTS OF CARNITINE AND ALKANOYL L-CARNITINES AND PROCESS FOR PREPARING SAME

The present invention relates to non-hygroscopic salts of L-carnitine and alkanoyl L-carnitines having the general formula;

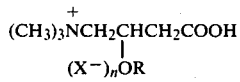

wherein
- $X^-$ is an anion of acid aspartate, acid citrate, acid phosphate, acid fumarate, lactate, acid maleate, acid oxalate, acid sulphate or orotate;
- R is hydrogen, provided that $X^-$ is other than the orotate anion, or lower alkanoyl selected among acetyl, propionyl and butyryl; and
- n is $\frac{1}{2}$ if $X^-$ is orotate, and 1 if $X^-$ is one of the other anions.

This invention also relates to a process for manufacturing such salts and to pharmaceutical compositions containing same.

It is well known that carnitine and its alkanoyl derivatives lend themselves to various therapeutical uses. It is also known that the salts of carnitine and of its alkanoyl derivatives possess the same therapeutical activities as those of the so-called "inner salts" and can, therefore, be used in place thereof, provided that they are "pharmacologically acceptable" salts. From the practical point of view, the choice between the "inner salt" and a true carnitine or alkanoyl carnitine salt depends mostly on which compound is more easily or economically available and on pharmaceutical technology considerations rather than on therapeutical activity considerations.

It should be understood that, as far as the present invention is concerned, the utility of the foregoing salts does not consist in a therapeutic activity qualitatively or quantitatively different from the activities already known, but rather in their lack of hygroscopicity in comparison with the corresponding inner salts and chlorides, and in the higher pH of their solutions as compared with the pH of the solutions of the corresponding chlorides. Because of their lack of hygroscopicity, these salts can be more easily handled and compounded, particularly with regard to the manufacture of solid administration forms, while the lower acidity of their solutions permits these salts to be used for preparing parenterally administrable forms, particularly via the intravenous route.

It is surprising and unexpected that the salts of L-carnitine and of alkanoyl L-carnitines according to this invention are not hygroscopic, because some corresponding salts of the racemic D,L form are known which are extremely hygroscopic and there is no theoretical ground for believing that, if a certain salt of D,L-carnitine or alkanoyl D,L-carnitine is hygroscopic, the same salt of the separated optical isomers, particularly the salt of the L-isomer, should not be hygroscopic as well. Thus, e.g., while the known salts D,L-carnitine acid fumarate and D,L-carnitine acid oxalate (see Chem. Abst. 60, 12097, 1964) are hygroscopic, the corresponding novel salts of this invention, L-carnitine acid fumarate and L-carnitine acid oxalate, are practically non-hygroscopic.

It is also surprising and unexpected (since there are no theorical grounds for holding the contrary true) that when a certain salt of L-carnitine is hygroscopic, the corresponding salt of alkanoyl L-carnitine should not be hygroscopic as well. Finally, it is surprising and unexpected that when the L-carnitine salt with a certain polybasic acid is hygroscopic, the acid salt of L-carnitine or alkanoyl L-carnitine with the same polybasic acid is not hygroscopic at all. Thus, for example, whereas the known L-carnitine phosphate is hygroscopic (see Medical Journal of Osaka University, 21, No. 1, December 1970, pages 7-12), the corresponding novel salts according to this invention, L-carnitine acid phosphate, and acetyl L-carnitine acid phosphate are not hygroscopic.

The process for producing the salts according to this invention comprises:
(a) converting in a per se known manner a chloride of the general formula;

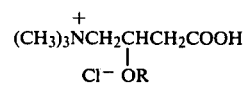

wherein R has the previously defined meaning, to the corresponding inner salt;

(b) reacting an aqueous or alcoholic solution of said inner salt at a temperature between room temperature and about 50° C., with an equimolar amount of aspartic, citric, phosphoric, fumaric, lactic, maleic, oxalic or sulphuric acid, or with a semi-molar amount of orotic acid, thus obtaining the desired salt; and (c) isolating the desired salt by concentration of the alcoholic solution, or concentration or lyophilization of the aqueous solution, and optionally subsequent crystallization.

As stated before, the conversion of the chloride in step (a) to the corresponding inner salt can be carried out via known procedures. For instance, a typical procedure is described by E. Strack in "Darstellung von O-acyl-carnitinen", Hoppe-Seyler's Z. Physiol. Chem., 351, 95-98, January 1970. Alternatively, the conversion can be carried out as disclosed in the Italian patent application 24432A/82 jointly filed on Nov. 25, 1982 by SIGMA-TAU Industrie Farmaceutiche Riunite S.p.A. and DE NORA S. A.

The following non-limiting examples illustrate the preparation of some non-hygroscopic salts according to the present invention.

EXAMPLE 1

Preparation of L-carnitine acid phosphate (ST 521)

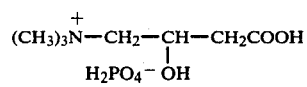

L-carnitine inner salt (200 g; 1.2 moles) was dissolved in the least necessary amount of water. To this solution 86% $H_3PO_4$ (61 ml; 1.2 moles) was added; the solution was then concentrated under vacuum and the residue was crystallized from isopropanol. The title compound was obtained as a non-hygroscopic solid.

$[\alpha]_D^{25} = -20$ (C=1 $H_2O$)

pH=3

M.P. 145°–150° C. (softening at 80° C.)
NMR D₂O δ4.5

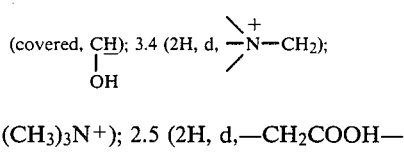

(covered, C$\underline{H}$); 3.4 (2H, d, $-\overset{+}{\underset{|}{N}}-CH_2$);
   OH 3.2 (9H, s, (CH₃)₃N⁺); 2.5 (2H, d, —CH₂COOH—).

EXAMPLE 2

Preparation of acetyl L-carnitine acid L-aspartate (ST 450)

Acetyl L-carnitine inner salt (7.2 g; 0.035 moles) was dissolved in water (50 cc). To the solution L-aspartic acid (4.7 g; 0.035 moles) was added and the solution was diluted with water to 800 cc. A complete dissolution of the mixture was obtained. The solution was lyophilized. A non-hygroscopic residue was obtained (11 g) consisting of the acetyl L-carnitine salt with aspartic acid.

$[\alpha]_D^{25} = -17.2$ (C=1, H₂O)
pH=3.5 5% H₂O solution
NMR D₂O δ5.5

(1H, m, —C$\underline{H}$—); 4.0–3.5 (3H, —C$\underline{H}$—; $\overset{+}{N}$—CH₂—);
  |                                     |
  O                                    NH₂

3.2 (9H, s, CH₃—$\overset{+}{N}$); 3.9–2.5 (4H, m, —CHC$\underline{H}_2$; —C$\underline{H}_2$COOH).
         |                                      |
         CH₃                                   NH₂ crystallized from isoprOH/Et₂O M.P. 190°–195° C.

EXAMPLE 3

Preparation of acetyl L-carnitine acid citrate (ST 455)

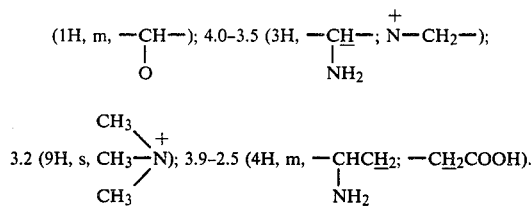

A solution of acetyl L-carnitine chloride (2.4 g; 0.01 moles) in methanol was kept under stirring with Amberlite 26 activated in OH⁻ form (14 g) for 48 hours. The disappearance of the chloride ions from the methanol solution was checked. Monohydrated citric acid (2.1 g; 0.01 moles) was then added. The solution was concentrated to dryness under vacuum. 4.5 grams of a non-hygroscopic product consisting of the title compound were obtained.

NMR D₂O δ5.6

(1H, m, —C$\underline{H}$—); 3.8 (2H, m, $-\overset{+}{\underset{|}{N}}-CH_2-$);
   OCO 3.2 (9H, s, CH₃—$\overset{+}{N}$);
         |
         CH₃

2.9–2.7 (6H, s and d, OH$\underset{|}{\overset{|}{C}}\begin{matrix}CH_2COO^-\\CH_2COOH\end{matrix}$ ; —C$\underline{H}_2$COOH);

2.2 (3H, s, —COCH₃)
$[\alpha]_D^{25} = -16$ C=1 H₂O
pH=2.9 5% H₂O

EXAMPLE 4

Preparation of acetyl L-carnitine acid maleate (ST 456)

Acetyl L-carnitine inner salt (10.1 g; 0.05 moles) was dissolved in water. To this solution, maleic acid (5.8 g; 0.05 moles) was added. The solution was lyophilized. A hygroscopic solid was obtained which was repeatedly washed with anhydrous acetone. The residue was oven-dried under vacuum. 8 grams of the title compound as a non-hygroscopic solid were obtained.

$[\alpha]_D^{25} = -22$ (C=1 H₂O)
M.P.=120°–123° C.
pH=2.7 5% H₂O solution
NMR D₂O δ6.3 (2H, s, —CH=CH—);

5.6 (1H, m, —C$\underline{H}$—);
            |
            OCO—

3.8 (2H, m, $-\overset{+}{\underset{|}{N}}-CH_2-$); 3.3 (9H, s, CH₃—$\overset{+}{N}$);
                                                        |
                                                       CH₃

2.9 (2H, d, —C$\underline{H}_2$—COOH); 2.1 (3H, s, —COCH₃)

| H.P.L.C. | |
|---|---|
| column | licrosorb NH₂ |
| detector | U.V. 205 nm |
| mobile phase | (NH₄)₂HPO₄ 0.01M—CH₃CN (40–60) pH 7.8 with H₃PO₄ conc. |
| pressure | 45 atm. |
| flow rate | 2 ml/min |
| chart speed | 0.5 cm/min |
| R$_F$ | acetyl carnitine 1.0 cm |
| | maleic acid 1.5 cm |

EXAMPLE 5

Preparation of acetyl L-carnitine acid phosphate (ST 451)

$$(CH_3)_3-\overset{+}{N}CH_2-\underset{H_2PO_4^-}{\underset{|}{CH}}-CH_2-COOH$$
$$\phantom{(CH_3)_3-\overset{+}{N}CH_2-}OCOCH_3$$

Acetyl L-carnitine inner salt (7.2 g; 0.035 moles) was dissolved in 50 cc of H₂O. To the resulting aqueous solution 85% H₃PO₄ (2.1 ml; 0.035 moles) was added. The aqueous solution was lyophilized and the residue was washed with anhydrous acetone. The product was dried under vacuum yielding 7.8 g of the non-hygroscopic title compound.

$[\alpha]_D^{25} = -17.7$ (C=1, H₂O)
M.P.=155°–157° C.
pH=2.75 5% H₂O solution
NMR D₂O δ5.6

(1H, m, —CH—); 3.8 (2H, m, $\diagdown\!\!\!\!{\overset{+}{\underset{\diagup}{N}}}$—CH$_2$—);
|
O 3.2 (9H, s, CH$_3$$\diagdown\!\!\!\!{\overset{+}{\underset{\diagup}{N}}}$—); 2.8 (2H, d, C$\underline{H}_2$COOH);
CH$_3$
CH$_3$ 2.2 (3H, s, —COCH$_3$)

| | C$_9$H$_{20}$NO$_8$P | |
|---|---|---|
| | Calculated | Found |
| C | 35.87 | 34.95 |
| H | 6.69 | 6.58 | Cl < 0.2% |
| N | 4.64 | 4.50 |
| P | 10.28 | 10.50 |

EXAMPLE 6

Preparation of acetyl L-carnitine acid fumarate (ST 468)

Acetyl L-carnitine inner salt (4.95 g; 0.025 moles) was dissolved in 100 cc of H$_2$O. To the resulting solution fumaric acid (2.82 g; 0.025 moles) was added and the solution was lyophilized. 3.5 grams of a solid consisting of non-hygroscopic acetyl L-carnitine acid fumarate were obtained.

$[\alpha]_D^{25} = -22.7$ (C=1 H$_2$O)
pH=3.3 0.5% H$_2$O solution
NMR D$_2$O δ6.6 (2H, s, —C$\underline{H}$=C$\underline{H}$—);

5.5 (1H, m, —CH—);
|
O 3.8 (2H, m, $\diagdown\!\!\!\!{\overset{+}{\underset{\diagup}{N}}}$—CH$_2$—);

3.2 (9H, s, (CH$_3$)$_3$N$^+$—); 2.6 (2H, d, —CH$_2$COO); 2.1 (3H, s, —COC$\underline{H}_3$).
M.P. 159°–161° C.

EXAMPLE 7

Preparation of propionyl L-carnitine acid fumarate (ST 522)

Propionyl L-carnitine chloride (2.67 g; 0.01 moles) was dissolved in 10 cc of H$_2$O and the solution eluted through a column of IRA 402 Amberlite resin activated in HCO$_3^-$ form (20 cc). 80 cc of an aqueous solution containing propionyl L-carnitine inner salt were collected. To this solution, fumaric acid (1.16 g; 0.01 moles) dissolved in 20 cc of H$_2$O was added. The solution was heated to 50° C. and kept at this temperature for 1 hour. The solution was then lyophilized. The lyophilized product was crystallized from isopropanol. The title compound was obtained as a non-hygroscopic solid.

$[\alpha]_D^{25} = -20.9$ (C=1 H$_2$O), M.P. 122°–125° C.
NMR D$_2$O δ6.6 (2H, s, —CH=CH—); 5.6 (1H, m,

—CH—);
|
O—

3.8 (2H, m, —N$^+$—CH$_2$—); 3.3 (9H, s, (CH$_3$)$_3$N$^+$);
2.8–2.3 (4H, m, —C$\underline{H}_2$COOH; —C$\underline{H}_2$CH$_3$); 1.2 (3H, t, CH$_2$C$\underline{H}_3$)

| | C$_{14}$H$_{23}$O$_8$N | |
|---|---|---|
| | Calculated | Found |
| C % | 50.44 | 49.80 |
| H % | 6.95 | 7.32 |
| N % | 4.20 | 4.05 |

EXAMPLES 8–10

By following the procedures of the previous examples, the following salts were prepared, whose melting point and optical rotatory power are indicated.

Example 8: L-carnitine acid fumarate
M.P. 137°–139° C. (in ethanol)
$[\alpha]_D^{20} = -16$ (C=2.5 H$_2$O)
Example 9: L-carnitine acid oxalate
M.P. 115°–118° C. (in ethanol)
$[\alpha]_D^{20} = -20$ (C=2.5 H$_2$O)
Example 10: L-carnitine acid sulphate
M.P. 109°–113° C. (in ethanol)
$[\alpha]_D^{20} = -18.5$ (C=2.5 H$_2$O)

It was found that all the compounds of the Examples 8–10 were non-hygroscopic.

EXAMPLE 11

Preparation of propionyl L-carnitine orotate (ST 552)

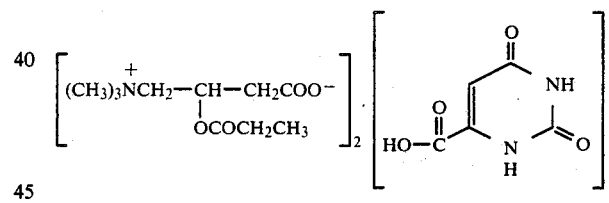

Propionyl L-carnitine inner salt (42.4 g; 0.2 moles) and orotic acid (17.4 g; 0.1 moles) were dissolved in methanol (200 cc). The solution was stirred at room temperature for about 1 hour and then concentrated to dryness under vacuum. A white solid consisting of the salt of propionyl L-carnitine with orotic acid (2:1 ratio) was obtained.

| HPLC VARIAN | |
|---|---|
| Column: | μ Bondapak NH$_2$ |
| eluent: | KH$_2$PO$_4$ 0.05M 35 |
| | CH$_3$CN 65 |
| pressure: | 60 atm. |
| flow rate: | 1.5 ml/min |
| U.V. detector: | 205 λ |
| integrator: | 4270 Varian |
| chart speed: | 0.5 cm/min. |
| orotic acid: | RF 2.70 cm |
| Propionyl L-carnitine: | Rf 4.95 cm |

The ratio between orotic acid and propionyl L-carnitine (calculated from the ratio of the surface areas with reference to a standard) proved to be 32%:78%, whereas the theoretical value calculated for the salt consisting of 2 moles of propionyl carnitine and 1 mole of orotic acid is 29%:71%. The salt proved to be hydro-soluble forming a 5% solution. This solution was stable for about 24 hours.

$[\alpha]^{25} = -23$ (H$_2$O)

NMR D$_2$O δ6.3

(1H, s, [N–H / N–O structure] ); 5.8 (2H, m, (—CH—)$_2$);

3.9 (4H, m, (N$^+$—CH$_2$)$_2$); 3.3 (18H, s, ((CH$_3$)$_3$N$^+$)$_2$); 2.9 (4H, d, (CH$_2$CO)$_2$); 2.6 (4H, q, (OCOCH$_2$—)$_2$); 1.3 (6H, t, (—CH$_3$)$_2$).

EXAMPLES 12-13

By following the procedures of Example 11, the following salts were prepared. Their optical rotatory power is hereinbelow indicated:

Example 12: acetyl L-carnitine orotate
$[\alpha]_D^{20} = -25$

Example 13: butyryl L-carnitine orotate
$[\alpha]_D^{20} = -15$

The present invention further comprises pharmaceutical compositions containing at least one of the previously mentioned non-hygroscopic salts as the active constituent, and a pharmacologically acceptable solid or liquid excipient. In particular, the solid compositions which are suitable for preparing orally administrable dosage forms are preferred. For instance, a composition suitable for manufacturing tablets is the following:

| | |
|---|---|
| L-carnitine non hygroscopic salt according to the invention | mg 500 |
| Starch | mg 20 |
| Talc | mg 10 |
| Ca-stearate | mg 1 |
| | mg 531 |

The following is a composition suitable for manufacturing capsules:

| | |
|---|---|
| L-carnitine non-hygroscopic salt according to the invention | mg 380 |
| Lactose | mg 50 |
| Starch | mg 20 |
| Talc | mg 5 |
| Ca-stearate | mg 2 |
| | mg 457 |

I claim:

1. L-carnitine and alkanoyl L-carnitine non-hygroscopic salts of the general formula:

$$(CH_3)_3\overset{+}{N}CH_2CHCH_2COOH$$
$$\underset{(X^-)_n OR}{|}$$

wherein

X$^-$ is an anion selected from the group consisting of acid aspartate, acid citrate, acid phosphate, acid fumarate, lactate, acid maleate, acid oxalate, acid sulphate and orotate anions;

R is hydrogen provided that X$^-$ is other than orotate, or is acetyl, propionyl or butyryl; and n is ½ is X$^-$ is orotate, and 1 if X$^-$ is one of the other anions.

2. A pharmaceutical composition comprising a salt of claim 1 as the active constituent and a pharmacologically acceptable solid or liquid excipient therefor.

3. The composition of claim 2 in solid form.

4. A salt according to claim 1 which is L-carnitine phosphate in substantially non-hygroscopic form.

5. A salt according to claim 1 which is acetyl L-carnitine L-aspartate in substantially non-hygroscopic form.

6. A salt according to claim 1 which is acetyl L-carnitine citrate in substantially non-hygroscopic form.

7. A salt according to claim 1 which is acetyl L-carnitine maleate in substantially non-hygroscopic form.

8. A salt according to claim 1 which is acetyl L-carnitine phosphate in substantially non-hygroscopic form.

9. A salt according to claim 1 which is acetyl L-carnitine fumarate in substantially non-hygroscopic form.

10. A salt according to claim 1 which is propionyl L-carnitine fumarate in substantially non-hygroscopic form.

11. A salt according to claim 1 which is L-carnitine fumarate in substantially non-hygroscopic form.

12. A salt according to claim 1 which is L-carnitine oxalate in substantially non-hygroscopic form.

13. A salt according to claim 1 which is L-carnitine sulfate in substantially non-hygroscopic form.

14. A salt according to claim 1 which is propionyl L-carnitine orotate in substantially non-hygroscopic form.

15. A salt according to claim 1 which is acetyl L-carnitine orotate in substantially non-hygroscopic form.

16. A salt according to claim 1 which is butyryl L-carnitine orotate in substantially non-hygroscopic form.

* * * * *